(12) United States Patent
Wang

(10) Patent No.: US 9,273,012 B2
(45) Date of Patent: Mar. 1, 2016

(54) FACILE PREPARATION OF 4-SUBSTITUTED QUINAZOLINES AND RELATED HETEROCYCLES

(75) Inventor: Zerong Daniel Wang, Houston, TX (US)

(73) Assignee: University of Houston System, Houston, TX (US)

(\*) Notice: Subject to any disclaimer, the term of this patent is extended or adjusted under 35 U.S.C. 154(b) by 13 days.

(21) Appl. No.: 13/459,297

(22) Filed: Apr. 30, 2012

(65) Prior Publication Data
US 2012/0283436 A1     Nov. 8, 2012

Related U.S. Application Data

(60) Provisional application No. 61/481,804, filed on May 3, 2011.

(51) Int. Cl.
| | |
|---|---|
| *C07D 239/74* | (2006.01) |
| *C07D 239/70* | (2006.01) |
| *C07D 487/06* | (2006.01) |

(52) U.S. Cl.
CPC ............ *C07D 239/74* (2013.01); *C07D 239/70* (2013.01); *C07D 487/06* (2013.01)

(58) Field of Classification Search
CPC .................................................. C07D 239/74
See application file for complete search history.

(56) References Cited

U.S. PATENT DOCUMENTS

2005/0096327 A1\*   5/2005   Caprathe et al. ......... 514/252.17

FOREIGN PATENT DOCUMENTS

| WO | WO 2008012326 A1 \* | 1/2008 |
|---|---|---|
| WO | WO 2008020302 A2 \* | 2/2008 |

OTHER PUBLICATIONS

Jensen, W.B. "A Note on the Term 'Chalcogen.'" Journal of Chem. Ed. (Sep. 1997), vol. 74, No. 9, pp. 1062-1064.\*

\* cited by examiner

*Primary Examiner* — Noble Jarrell
*Assistant Examiner* — John S Kenyon
(74) *Attorney, Agent, or Firm* — Jackson Walker L.L.P.

(57) ABSTRACT

A straightforward single step method for the preparation and/or production of substituted quinazolines is disclosed, wherein said quinazolines preferably contain one substituent at position 4, and may contain other functional groups at various positions, such as 5, 6, 7, and/or 8 of quinazolines. In addition, the extension of this new method leads to the formation of different type of heterocyclic aromatic compounds, that include but are not limited to perimidines, anthrapyrimidin-7-ones (also known as anthrapyrimidinones), anthra[1,9:5,10]dipyrimidines (also known as quinazoline[5,4-ef]perimidines) and benzo[e]-pyrimido[4,5,6-gh]pyrimidines.

6 Claims, 5 Drawing Sheets

$R_1$, $R_{18}$ = H, F, Cl, Br, I, $NO_2$, $CF_3$, alkyl, aryl $R_2$ = aryl, alkyl of less than two α-hydrogen atom or any other groups that can survive under the reaction condition.

FACILE PREPARATION OF 4-SUBSTITUTED QUINAZOLINES AND RELATED HETEROCYCLES

CROSS-REFERENCE TO RELATED APPLICATIONS

This applications claims priority to U.S. Provisional Patent Application Ser. No. 61/481,804, filed May 3, 2011, which is hereby incorporated by reference for all purposes.

FIELD

Disclosed herewith a unique, general and simple method to make, prepare and/or to produce substituted quinazolines that contain a substituent at position 4, and may or may not contain functional groups at other positions of the fused benzene ring within the quinazoline structure scaffold, such as at position 5, 6, 7, and/or 8 of quinazolines. The said functional groups at these positions may be individual groups, or fused aromatic rings. However, the substituent at position 4 may be an aromatic or a non-aromatic functional group. If the functional group at position 4 is an aromatic group, it may further contain a variety of substituents on it; whereas for those non-aromatic groups at position 4, the non-aromatic groups could be alkyl group or other common functional groups. Although the alkyl group may be any possible alkyl group, it should not carry more than two α-hydrogens and preferably carries only one α-hydrogen or does not carry α-hydrogens at all.

BACKGROUND

Quinazolines, being one type of nitrogenous heterocycles, have been identified with a variety type of biological activities, such as analgesic [1 (Note: bracketed numerals used herein relate to listed references appearing below within the Detailed Description Of Illustrative Embodiments)], antibacterial [2], antibiotic [1(b)], anticonvulsant [1(a),2(b),3], antidepressant [4], anti-inflammatory [1(a), 3, 5], anti-hypertensive [1(b), 3], antimalarial [2(a), 6], antineoplastic [2(a)], antitumoral [1(b), 7] as well as diuretic [1(b), 3], genotoxic [8], hypoglycemic [1(b)], narcotic [1(b)], sedative activities [1(b)] etc. Thus, the quinazoline derivatives have been applied as inhibitors for dihydrofolate reductase [2(a), 6], epidermal growth factor receptor [3, 7, 9], NADH-quinone reductase [10], TNF-α production [11], as well as T cell proliferation [11-12]. As a result, many pharmaceutical compounds containing quinazoline moiety have been widely applied for medicines.

For example, Alfuzosin is used in men to treat symptoms of an enlarged prostate [13], so-called benign prostatic hyperplasia [14]. Doxazosin, with structure and activity similar to Alfuzosin, is also used in men to treat the symptoms of an enlarged prostate [13-14]. Gefitinib is used to treat non-small cell lung cancer in people who have already been treated with other chemotherapy medications whereas whose conditions have not been improved or even become worse [9(a), 15]. Erlotinib, with a structure similar to Getifinib, is also used to treat non-small cell lung cancer that has spread to the nearby tissues or to other parts of the body in patients who have already been treated with at least one other chemotherapy medication without obvious improvement [16]. Lapatinib is used to treat a certain type of advanced breast cancer in people who have already been treated with other chemotherapy medications [17].

In comparison, perimidine derivatives, with an extended aromatic system larger than quinazolines, have also been identified with a variety type of biological activities, such as antibacterial and antifungal activity [18], cytotoxic effect and in vivo immunosuppressant and immunostimulant activity [19], and have been applied as antagonists for nonpeptide corticotropin releasing factor (CRF) receptor [20]. In addition, perimidines usually absorb light of longer wavelength that could be stretched to the range of visible light and even to near-infrared range [21]. Thus, perimidines may appear in different colors, depending on the conjugated aromatic system as well as the functional groups they carry. As a result, perimidines have been developed as colorants, dyes and pigments [22].

Due to the wide applications of quinazolines as well as perimidines, a variety type of synthetic or preparative methods have been developed to make these type of heterocycles, according to the available starting materials and the structures of final products with different functional group distributions. Among these synthetic or preparative methods for quinazoline derivatives, a large portion of methods are focused on the introduction of the desired functional group into the existing quinazoline core-structure, which are not related to the current disclosure. In addition, even though there are still many synthetic methods for quinazoline derivatives that have a functional group attached to position 4 of quinazoline moiety through a heteroatom, such as oxygen, nitrogen, sulfur, etc., or with a functional group as simple as hydroxyl (OH), amino ($NH_2$), or halogen (F, Cl, Br, I), these methods are in fact not related to the current disclosure either.

There is a need for a general, simple and direct method for the preparation and/or manufacturing of quinazoline derivatives that carry one substituent at position 4 of quinazoline ring via a carbon atom attachment, and may contain other functional groups at the rest positions of quinazoline rings, except for position 2 of the quinazoline ring where no other functional group rather than hydrogen is attached. This direct method for the preparation of quinazoline derivatives also includes or is applicable to the preparation and/or manufacturing of even largely fused quinazoline derivatives that include perimidines, anthrapyrimidine-7-one, anthra[1,9:5,10]dipyrimidine and benzo[e]pyrimido[4,5,6-gh]pyrimidine when different 1-amino-9H-fluoren-9-ones, aminoanthraquinones are used as the starting materials. Likewise, only those methods for the preparation of perimidines, such as anthrapyrimidine-7-ones, anthra[1,9:5,10]dipyrimidines and benzo[e]pyrimido[4,5,6-gh]pyrimidines, which are closely related to the disclosed method will be compared below.

The preparation of quinazoline derivatives with a carbon-attached substituent at position 4 may be classified into several groups as described below, using 4-phenylquinazoline as in the following examples:

a) The preparation of 4-phenylquinazolines from an N-benzylideneaniline type of Schiff base that is formed from aniline and benzaldehyde, as shown in the reaction between p-chloro-(α-chlorobenzylidene)aniline and benzonitrile in 1,4-dichlorobenzene at 140° C. in the presence of $AlBr_3$ that afforded 69% of 6-chloro-2,4-diphenylquinazoline [23], and the reaction between N-[o-(triphenylphosphoranylideneamino)benzylidene]-p-toluidine and p-nitrobenzaldehyde when refluxed in xylene for 12 hours that gave 70% of 6-methyl-4-p-nitrophenyl-2-phenylquinazoline [24]. The latter reaction would afford dihydroquinazolines as well if other benzaldehydes rather than p-nitrobenzaldehyde are used. In addition, the reaction between 3,4-diphenyl-1,2,4-oxadiazol-5(4H)-one and benzylideneaniline also afforded 2,4-diphenylquinazoline [25];

b) The preparation of 4-phenylquinazolines from amidobenzenes or benzonitriles, as shown in the reaction when p-chloropivalamidobenzene was dilithiated with n-BuLi followed by the addition of o-fluorobenzonitrile to give 57% of 2-t-butyl-6-chloro-4-o-fluorophenylquinazoline [26], and the treatment of o-aminobenzonitrile with phenylmagnesium halide from which the resulting intermediate 2-$H_2NC_6H_4C$(Ph)=N$^-$ then cyclized with carbonyl compounds (e.g., acid chlorides, anhydrides, formates) to give 4-phenyl-quinazolines [27]. Alternatively, the reaction between benzanilides and benzonitriles in the presence of $PCl_5$ and $AlCl_3$ in $PhNO_2$ at 120-150° C. also afforded 2,4-diphenylquinazoline [28];

c) The reaction between benzenediazonium salt and benzonitrile, as shown in the reaction between o-benzylbenzenediazonium tetrafluoroborate and benzonitrile that gave 53% of 8-benzyl-2,4-diphenylquinazoline [29];

d) The conversion of benzo[e][1,4]diazepine derivatives into 4-phenyl-quinazolines, such as the refluxing of 3-hydroxy-5-phenyl-3H-1,4-benzodiazepin-2(1H)-one in AcOH to give 35% of 4-phenyl-2-quinazolinecarbaldehyde [30], thermolysis of 7-chloro-3-(2-methylimidazol-1-yl)-5-phenyl-3H-1,4-benzodiazepin-2-amine in 50% $H_2SO_4$ that afforded about 15% of 6-chloro-4-phenyl-2-quinazolinecarbaldehyde [31], thermolysis of 7-bromo-3-hydroxy-5-pyridin-2'-yl-3H-1,4-benzodiazepin-2(1H)-one at 220° C. to give 6-bromo-4-pyridin-2'-yl-2-quinazolinecarbaldehyde [32], sublimation of 7-chloro-5-phenyl-1,3-dihydro-2,1,4-benzothiadiazepine 2,2,4-trioxide at 160° C. under vacuum (at $10^{-3}$ mmHg) to give 6-chloro-4-phenylquinazoline [33], acidic hydrolysis of 8-chloro-6-phenyl-3,4-dihydro-1,5-benzodiazocin-2-amine in refluxing methanolic hydrogen chloride for 2.5 hours to afford 53% of 2-α-aminoethyl-6-chloro-4-phenylquinazoline [34], treatment of 8-chloro-3-methyl-6-phenyl-3H-4,1,5-benzoxadiazocin-2(1H)-one with sodium methoxide for 20 hours to yield 50% of 2-acetyl-6-chloro-4-phenylquinazoline [35], oxidation of N-methyl-7-nitro-5-phenyl-1H-1,4-benzodiazepine-3-carboxamide with $CrO_3$ in AcOH to give 29% of N-methyl-6-nitro-4-phenyl-2-quinazolinecarboxamide [36], and hydrogenation of 8-chloro-6-phenyl-3H-4,1,5-benzoxadiazocin-2(1H)-one oxime over Raney-nickel to afford 50% of 6-chloro-2-hydroxymethyl-4-phenylquinazoline [37];

e) Thermolysis of 1,3,6-triphenyl-1,4-dihydro-1,2,4,5-tetrazine at 200° C. to a mixture of three components that included 2,4-diphenylquinazoline [38];

f) The reaction between 3-phenylbenzo[c]isoxazole and 5-methoxy-3-phenyl-2,4-imidazolidinedione in refluxing dioxane containing $TiCl_4$ as catalyst to give 82% of 4,N-diphenyl-2-quinazolinecarboxamide [39];

g) Isomerization of 7-chloro-5-hydroxy-5-phenyl-1,2,3,5-tetrahydropyrrolo[1,2-a]-quinazolin-1-one into 2-α-carboxyethyl-6-chloro-4-phenylquinazoline in ~45% yield under basic condition [40];

h) The conversion of benzotriazene derivatives into 4-phenyl quinazolines, such as the transformation of 1,2-diaryl-2-(benzotriazol-1-yl)enamines prepared from lithiated (α-arylbenzotriazol-1-yl)methane and nitriles to afford 2,4-arylquinazolines, and the reaction between 2-(benzotriazol-1-yl)-1,2-diphenylethanone and formamide at 150° C. to afford 50% of 2,4-diphenylquinazoline [41]; and i) the treatment of 1-amino-4-methyl-9H-thioxanthen-9-one 10,10-dioxide with formic acid-formamide at 180° C. for 3 hours to give a mixture of products from which 6-methyl-4-phenylquinazoline was isolated in low yield [42].

Although these known methods listed from a) to i) all lead to the formation of 4-phenylquinazolines, they are quite different from the presently disclosed method, because the cited methods mentioned above all afford 4-substituted quinazolines with an additional functional group at position 2 through a carbon-carbon attachment for which the removal of such group might prove difficult to accomplish.

Only the following several methods are of a kind of similarity to the presently disclosed method, to an extent, that all use 2-aminobenzophenone as the starting material. These similar synthetic methods include the reaction between 2-aminobenzophenone and ethyl carbamate and further treatment with phosphoryl trichloride [43], thermal reaction between 2-aminobenzophenone and formamide [44], the reaction between hydroxyglycine and 2-aminobenzophenones to give 1,2-dihydro-4-phenylquinazoline-2-carboxylic acids which is then converted into the corresponding quinazoline derivatives via air oxidation [45], and the treatment of 2-aminobenzophenone with urotropine and ethyl bromoacetate in alcohol to form a mixture of 4-phenylquinazoline and 4-phenyl-1,2-dihydroquinazoline [46].

For comparison, several methods have been developed for the preparation of aromatically-fused perimidine derivatives, including but not limited to anthrapyrimidine-7-ones, anthra[1,9:5,10]dipyrimidines and benzo[e]pyrimido-[4,5,6-gh]pyrimidines starting from aminoanthraquinones. Examples from such methods include the following:

a) a mixture of 1:2 ratio of 1-N-acetylaminoanthraquinone and phenol when treated with ammonia gas at a pressure of 5 atm at 125-130° C. afforded 2-methyl-1,9-anthrapyrimidine [47];

b) the thermal treatment of 1,5-diaminoanthraquinone-2-sulfonic acid with formamide followed by more than 10 times of 25% aqueous ammonia at 195-200° C. afforded diamino-1,9-anthrapyrimidine [48];

c) the reaction of 5-amino-4'-benzoylamino-1,1'-anthrimidecarbazole with 5 equivalents (by weight) of formamide and 10 equivalents of phenol for several hours formed 4'-benzoylamino-5,10-pyrimidino-1,1'-anthrimidcarbazole [49];

d) treatment of 7.8 parts of N,N-dimethyl-N'-[anthraquinoyl-(1)]-formamidinium chloride with 7.8 parts of ammonium acetate in 100 parts of glycol methyl monoether at 20° C. for 30 minutes gave 5.2 parts of 1,9-anthrapyrimidine, which could also be prepared by the treatment of 15.7 parts of N,N-dimethyl-N'-[anthraquinoyl-(1)]-formamidinium chloride with 14.4 parts of ammonium carbonate in 300 parts of methanol at 20° C. for 30 minutes which gave 10.6 parts of 1,9-anthrapyrimidine [50];

e) treatment of 50 parts of 1-dimethylformamidino-4-bromoanthraquinon-2-sulfonic acid with 25 parts (by weight) of an ammonium acetate in 800 parts of glycol monomethyl ether at 50° C. for 4 hours afforded 28 parts of 4-bromoanthrapyrimidin-2-sulfonic acid [51];

f) the reaction between 19.5 parts of 1,5-dihydroxy-4-propionylamino-8-aminoanthraquinone and 9.2 parts of dimethylformamide in 240 parts of chlorobenzene in the presence of 10.7 parts of thionyl chloride for 2 hours at 70° C., and the resulting product extracted with acetone was then treated with 30 parts of ammonium acetate in 250 parts of ethyleneglycol monomethyl ether at 75° C. for 4 hours to afford 18.2 parts of 1,5-dihydroxy-4-propionylamino-8,10-anthrapyrimidine [52]; and g) the reaction between 42.2 grams of 1,4-diamino-2,3-diphenoxy-anthraquinone and 31 grams of benzonitrile in 150 grams of trichlorobenzene in the presence of 34.4 grams of p-TsOH at 190° C. for 5-6 hours afforded 46.6 grams of 6-amino-2-phenyl-4,5-diphenoxy-anthrapyrimidine [53].

SUMMARY

The present disclosure provides a simple, direct and unique method to synthesize and/or produce quinazoline- and perimidine-based heterocycles. This disclosure covers the new method that involves the reaction between thiourea and a 2-aminobenzophenone or 2-aminoaryl aryl ketone or 2-aminoaryl alkyl ketone, in a solvent of high boiling point, and the composition of compounds prepared from this method.

The disclosed method for the preparation and/or production of substituted quinazolines results in quinazolines preferably containing one substituent at position 4, and may contain other functional groups at various positions, such as 5, 6, 7, and/or 8 of quinazolines. In addition, the extension of this new method leads to the formation of different type of heterocyclic aromatic compounds, that include but are not limited to perimidines, anthrapyrimidin-7-ones (also known as anthrapyrimidinones), anthra[1,9:5,10] dipyrimidines (also known as quinazoline[5,4-ef]perimidines) and benzo[e]-pyrimido[4,5,6-gh]pyrimidines.

The method includes a new chemical reaction between thiourea and a substituted 2-aminoaryl aryl ketone or a 2-aminoaryl alkyl ketone in a solvent of high boiling point. FIG. 1 depicts the structure of starting material in this disclosure. The moiety of 2-aminoaryl may be phenyl, substituted phenyl, naphthyl, and other aromatic rings, either heterocyclic aromatic or not, with an amino group at the ortho position; and the amino group may be a primary or secondary amino group.

For the case of 2-aminophenyl aryl ketones where the 2-aminoaryl moiety is 2-aminophenyl, the 2-aminophenyl moiety may also contain other functional groups such as bromo, chloro, fluoro, methyl, methoxy, nitro, acetyl, etc. at one or up to four positions of the 2-aminophenyl ring. In addition, the aryl moiety, on the other side of 2-aminophenyl ketone, may be any aromatic ring or fused aromatic ring, either homogeneous aromatic ring (such as phenyl, naphthyl, etc) or heterocyclic ring (such as pyridyl, pyrimidyl, etc).

For the case of aliphatic 2-aminoaryl ketones, the 2-aminoaryl moiety may be any possible aromatic structures that are similar to the ones described in the case of 2-aminoaryl aryl ketones; however, the aliphatic moiety alone should not react with thiourea, solvent or amino group, and will not help the enolization of the adjacent carbonyl group, so that the alkyl moiety preferably carries no more than one α-hydrogen atoms.

In addition, the reaction between thiourea and 1-amino-9H-fluoren-9-one, 1-aminoanthraquinone, 1,4-diaminoanthraquinone or 1,5-diaminoanthraquinone derivatives under the same condition affords perimidine derivatives, anthrapyrimidine-7-ones, anthra[1,9:5,10]dipyrimidines and bnezo[e]pyrimido[4,5,6-gh]perimidines. These perimidine derivatives may contain other functional groups at the rest positions of the aromatic rings. The functional group may be alkyl, aryl, bromo, chloro, fluoro, methoxyl, acetyl, etc. Likewise, the amino group in this series of starting materials may be a primary amino group (—$NH_2$) or secondary group (e.g., —$NHCH_3$, —$NHCOCH_3$, etc.).

Both quinazoline and perimidine derivatives have important applications in medicinal and pharmaceutical industries. In addition, the synthesized perimidine derivatives in this disclosure also have important applications in dye, colorant, and pigment industries.

BRIEF DESCRIPTION OF THE DRAWINGS

The features, nature, and advantages of the disclosed subject matter will become more apparent from the detailed description set forth below when taken in conjunction with the drawings, in which like references indicate like features and wherein.

DETAILED DESCRIPTION OF ILLUSTRATIVE EMBODIMENTS

Composition:

The disclosed subject matter provides a new method to make quinazoline-based heterocycles as well as perimidine- or anthrapyrimidine-based heterocycles, starting from the reaction between thiourea and any ketone compounds containing a structural scaffold of 2-aminoaryl moeity, in a solvent of high boiling point.

Figure 1:
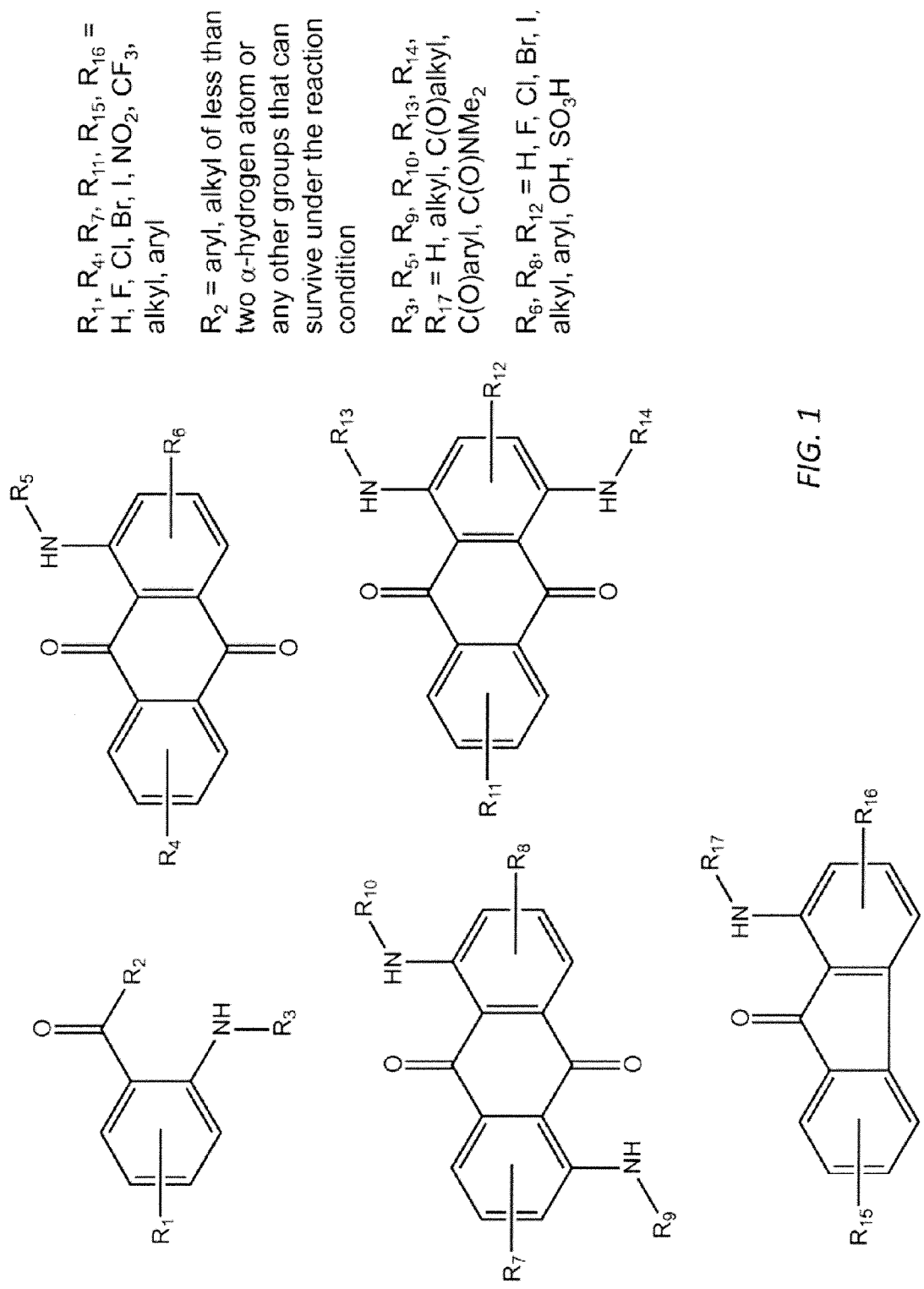
FIG. 1 depicts the structure of the starting materials for the presently disclosed preparation of 4-substituted quinazolines and related heterocycles.
Figure 2:
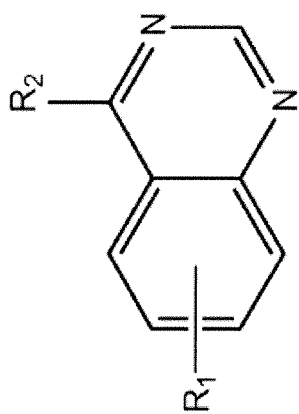
FIG. 2 shows the structures of quinazoline derivatives formed according to the teachings of the present disclosure.
Figure 2:
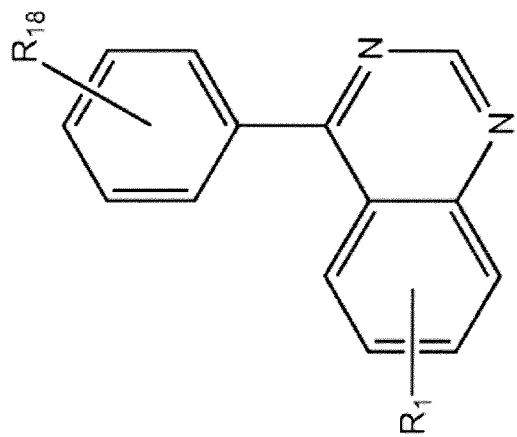

For the quinazoline-based heterocycles, they contain a general structure as outlined in FIG. 2, in which $R_1$ may be halogens (F, Cl, Br or I), or alkyl, aryl, $NO_2$, $CF_2$, etc. at any position among the four possible sites (5, 6, 7, or 8), and when $R_1$=aryl group, the aryl group may be attached to the quinazoline moiety with a single carbon-carbon bond at any position among the four binding sites, or fused to the quinazoline moiety. $R_{18}$ may be halogens (F, Cl, Br or I), or alkyl, aryl, $CO_2H$, etc. that are attached to any positions among the five possible binding sites (from 2' to 6'). Likewise, when $R_{18}$=aryl, the aryl group may be attached to the 4-phenyl ring either through a single carbon-carbon attachment to any carbon atom from 2' to 6', or fused to the 4-phenyl ring. $R_2$ should be an alkyl group containing less than two α-hydrogen atoms so that the alkyl group will not enolize with the adjacent carbonyl group before the ketone starting material is transformed into quinazoline. In addition, $R_2$ may also be any other functional groups that will not react with thiourea or amino group and can survive under the reaction condition.

Figure 3:
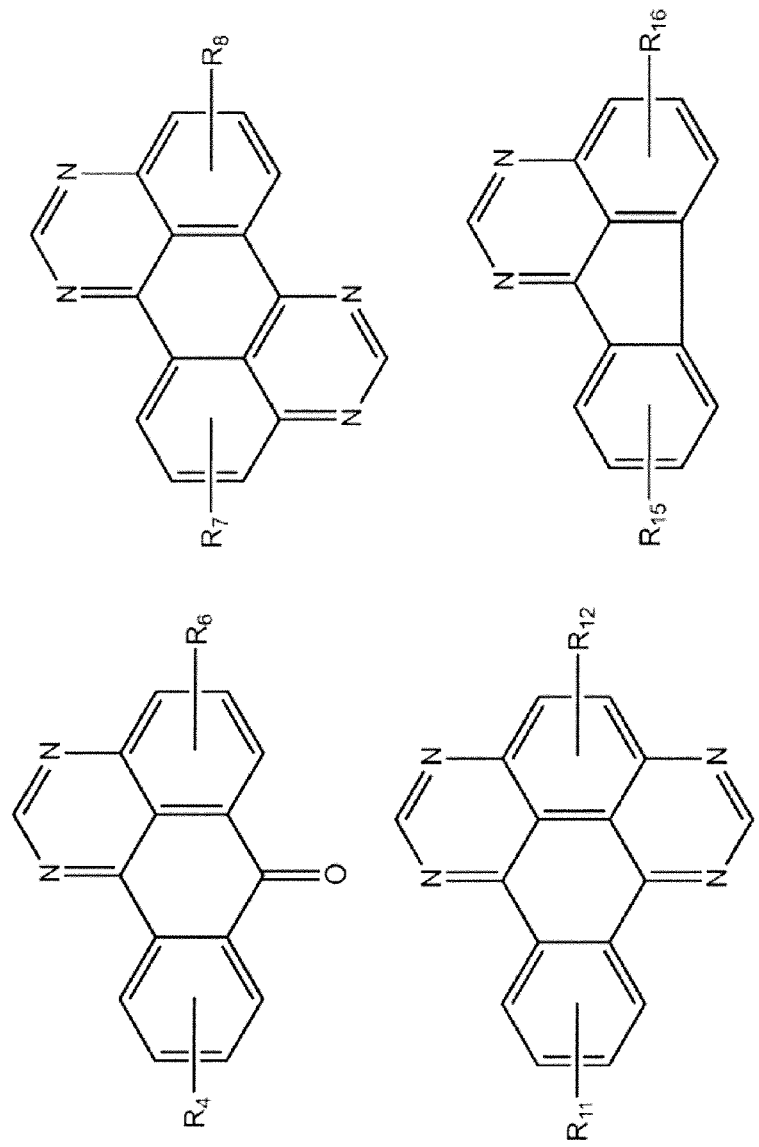
FIG. 3 illustrates structures of perimidine and anthrapyramidine series of heterocycles prepared according the disclosed subject matter.

For the perimidine- or anthrapyrimidine-based heterocycles, four general structures, i.e., perimidines, anthrapyrimidin-7-ones, anthra[1,9:5,10]dipyrimidines, and benzo[e] pyrimido[4,5,6-gh]pyrimidines, are shown in FIG. 3, in which $R_4$, $R_7$, $R_{11}$, $R_{15}$, and $R_{16}$ may be halogens (F, Cl, Br or I), or alkyl, aryl, OH, etc. at any position among the possible sites, and $R_6$, $R_8$ and $R_{12}$ may be halogens (F, Cl, Br or I), alkyl, aryl, OH, $SO_3H$, etc. at any position among the possible sites.

Figure 4:
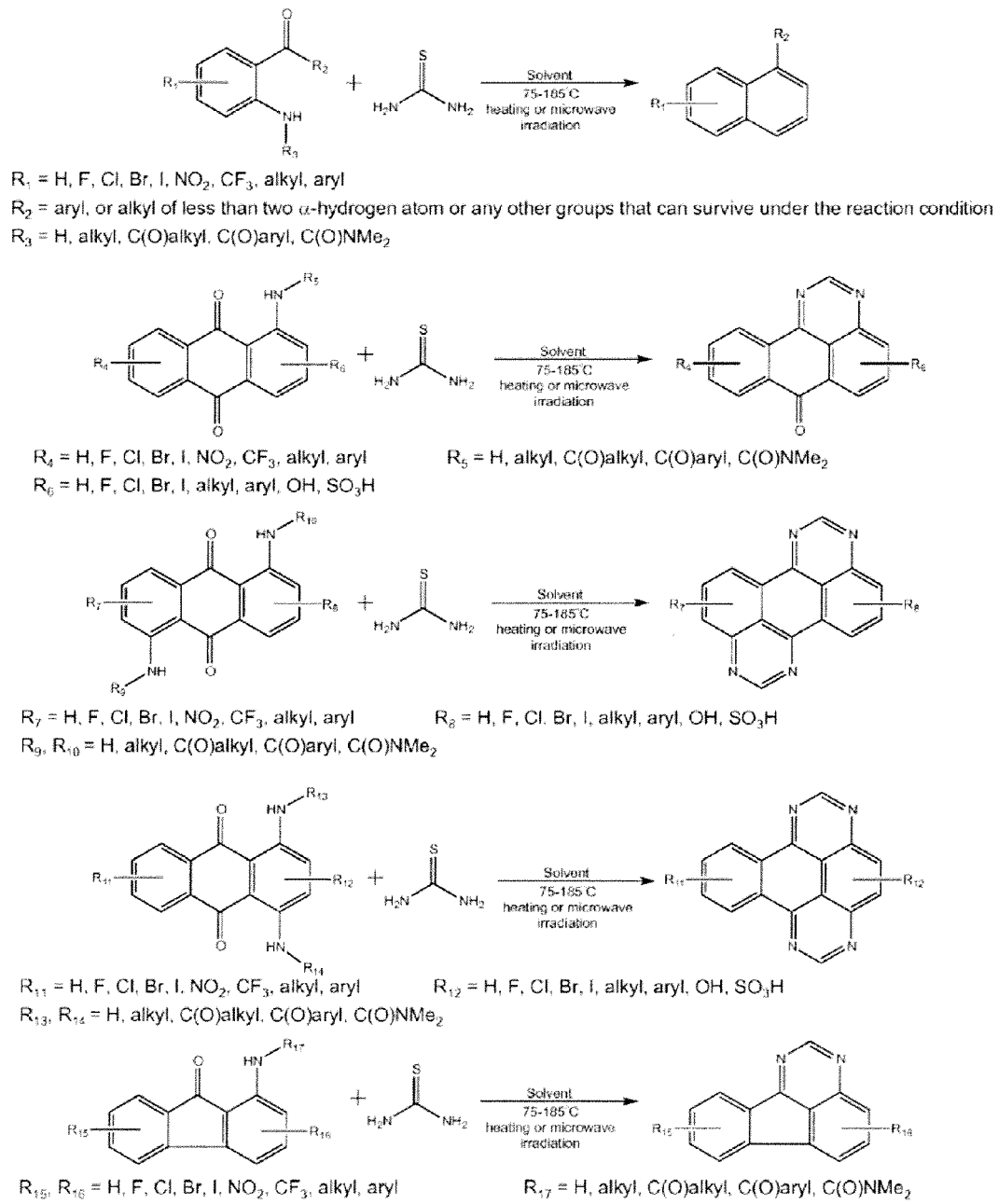
FIG. 4 provides a reaction flow according to the present disclosure for the preparation of heterocycles.

The disclosed subject matter provides a unique and simple method to prepare the heterocycles described above, involving a reaction between thiourea and an aryl ketone with an ortho amino group on the aryl ring that is heated in a solvent of high boiling point, as shown in FIG. 4. The solvents of high boiling points may be water (b.p. 100° C.), N,N-dimethylformamide (DMF, b.p. 153° C.), dimethyl sulfoxide (DMSO, b.p. 189° C.), ethylene glycol (b.p. 195-198° C.), 2-methoxyethanol (b.p. 124-125° C.), diethylene glycol monomethyl ether (b.p. 190-194° C.), p-dichlorobenzene (b.p. 173° C.), etc.

Among these possible solvents, DMSO would be the preferred solvent. The reaction may be carried out at a temperature in the range from 75° C. to 185° C., and preferably in the range from 110° C. to 165° C. The high reaction temperature for this reaction may be maintained through heating via heating mantle, oil bath, hot plate or even with hot air or other heat transmitting media, or via heating with microwave irradiation. A comparable yield of the heterocycle may be obtained under either reaction conditions, i.e., via heating or microwave irradiation, although the reaction carried out under microwave irradiation is more suitable for a relatively small-scale reaction (up to 20 mL).

Figure 5:
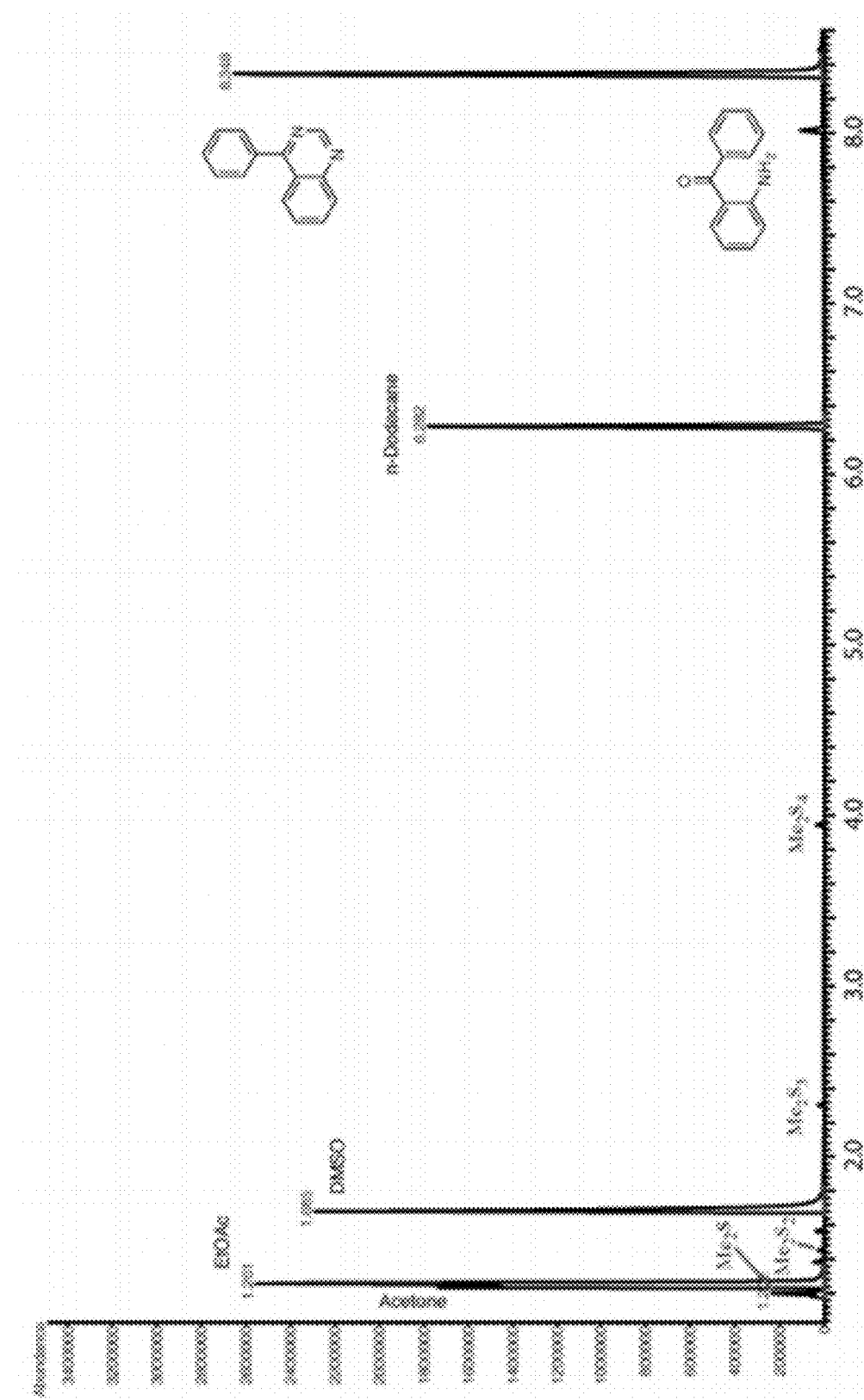
FIG. 5 displays gas chromatographic analysis results of a reaction mixture between thiourea and 2-aminobenzophenone in DMSO for analyzing reaction yield of the presently disclosed method.

Under the optimized reaction condition, the disclosed reaction usually affords quinazoline of yield up to 100%, according to GC/MS analysis, as shown in FIG. 5. Usually, a single product is formed. Therefore, the isolation of product is very simple and straightforward, where the formed product may crystallize directly from the reaction solvent when the reaction mixture is cooled down to room temperature. However, if no crystal forms, the product may be isolated with conventional methods.

In addition, the extension of this method starting from aminoanthraquinones under conditions similar to the ones to form quinazolines will form even enlarged aromatic heterocycles, that include perimidines, such as anthrapyrimidine-7-ones, anthra[1,9:5,10]dipyrimidines and benzo[e]pyrimido[4,5,6-gh]pyrimidines.

EXPERIMENTS OF THE DISCLOSURE

The structures of the presently disclosed facile preparation of 4-substituted quinazolines and related heterocycles are evidenced by the following examples:

Example 1

To a 20 mL microwave reaction vial with a micro magnetic stir bar, were added 0.460 g of 2-aminobenzophenone, 0.355 g of thiourea and 3.5 mL of DMSO. Then, the vial was sealed and heated with microwave at 155° C. for 5 hours. GC/MS analysis indicated that all 2-aminobenzophenone has been transformed into 4-phenyl-quinazoline as a single product. The reaction mixture was added to 25 mL of EtOAc and washed with water for three times and dried. The product was loaded on silica gel for column chromatography with hexane/EtOAc (5:1) as the eluent, affording an isolated yield of 4-phenyl-quinazoline greater than 85%.

Example 2

To a 25 mL round-bottomed flask were added 0.847 g of 2-aminobenzophenone, 0.658 g of thiourea and 6.0 mL of DMSO, and the mixture was heated at 155° C. for 5 hours. Work out of the reaction mixture by means of a method similar to Example 1 afforded 4-phenyl-quinazoline with a yield comparable to the reaction condition performed under microwave irradiation.

Example 3

To a one-drum vial were added 0.077 g of 2-aminobenzophenone, 0.060 g of thiourea and 0.35 mL of DMSO. Then the capped via was left on hot-plate at 155° C. for 5 hours, GC/MS analysis indicated that all 2-aminobenzophenone has been consumed and only 4-phenyl-quinazoline was identified as the product at 8.35 minutes when the GC was programmed from 100° C. (1 min) to 250° C. (2 min) at a speed of 20° C./min to raise the oven temperatures.

Example 4

To a 20 mL microwave reaction vial with a micro magnetic stir bar, were added 0.297 g of 2-amino-2',5-dichlorobenzophenone, 0.170 g of thiourea and 3 mL of DMSO. Then the vial was sealed and heated with microwave at 140° C. for 10 hours. The reaction mixture was worked out by dissolving in 25 mL of EtOAc and washed with water. As the reaction was heated at a lower temperature and worked out before its completion, the product was contaminated with the starting material so that silica gel column chromatography was used to purify the product, with hexane/EtOAc (5:1) as the eluent to afford 0.155 g of 2',6-dichloro-4-phenyl-quinazoline, in a yield of 50.5%.

The same reaction with 0.296 g of 2-amino-2',5-dichlorobenzophenone and 0.170 g of thiourea at 140° C. for 20 hours afforded 0.216 g of 2',6-dichloro-4-phenyl-quinazoline, after similar purification method, in a yield of 70.6%.

Example 5

To a 20 mL microwave reaction vial with a micro magnetic stir bar, were added 0.297 g of 2-amino-5-nitrobenzophenone, 0.186 g of thiourea and 3.0 mL of DMSO. Then the vial was sealed and heated with microwave at 140° C. for 20 hours. Two layers of liquid formed with brown liquid on the top and a dark brown gel like layer at the bottom. The reaction mixture was extracted with EtOAc and purified on column chromatography using hexane/EtOAc (5:1 to 4:1) as eluent, and 0.122 g of 4-phenyl-6-nitro-quinazoline was obtained, in a yield of 39.7%.

Example 6

To a 20 mL microwave reaction vial with a micro magnetic stir bar, were added 0.300 g of 1-aminoanthraquinone, 0.207 g of thiourea and 3 mL of DMSO. Then the vial was sealed and heated with microwave at 140° C. for 20 hours. A dark brown gel like mixture was obtained which was purified in a similar fashion with hexane/EtOAc (5:1 to 1:1) as the eluent, and 0.103 g of anthrapyrimidine was obtained, in a yield of 33.0%.

Example 7

To a 20 mL microwave reaction vial with a micro magnetic stir bar, were added 0.284 g of 2-amino-4-methylbenzophenone, 0.208 g of thiourea and 3 mL of DMSO. Then the vial was sealed and heated with microwave at 140° C. for 20 hours to form an orange liquid. The reaction mixture was treated in a similar method via column chromatography with hexane/EtOAc (6:1) as eluent to afford 0.293 g of 4-phenyl-7-methyl-quinazoline, in a yield of 99.0%.

Although the present disclosure is described with reference to specific embodiments, one skilled in the art could apply the principles discussed herein to other areas and/or embodiments without undue experimentation.

The subject matter of the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations based on the details of construction or design herein shown are intended, other than as described in the claims below. It is therefore evident that the particular illustrative embodiments disclosed above may be altered or modified, and all such variations are considered within the scope and spirit of the present disclosure.

REFERENCES

The following references are illustrative for highlighting the inventive subject matter of the present disclosure, wherein associated numerals relate to citation numbers discussed in the above Background section.

1. (a) Alagarsamy, V.; Shankar, D.; Solomon, V. R.; Sheorey, R. V.; Parthiban, P., Synthesis and Pharmacological Evaluation of 3-Cyclohexyl-2-substituted hydrazino-3H-quinazolin-4-ones as Analgesic and Anti-inflammatory Agents. *Acta Pharm.* 2009, 59, 75-88;
b) Mehta, S.; Swarnkar, N.; Vyas, M.; Vardia, J.; Punjabi, P. B.; Ameta, S. C., Synthesis and Characterization of Some Quinazoline Derivatives as Potential Antimicrobial Agents under Microwave Irradiation. *Bull. Korean Chem. Soc.* 2007, 28 (12), 2338-2342.
2. (a) Ashton, W. T.; Walker, F. C.; Hynes, J. B., Quinazolines as Inhibitors of Dihydrofolate Reductase. *J. Med. Chem.* 1973, 16, 694-697;
(b) Kamal, A.; Reddy, K. L.; Devaiah, V.; Shankaraiah, N.; Rao, M. V., Recent Advances in the Solid-Phase Combinatorial Synthetic Strategies for the Quinoxaline, Quinazoline and Benzimidazole Based Privileged Structures. *Mini-Reviews in Medicinal Chemistry*, 2006, 6, 71-89.
3. Connolly, D. J.; Cusack, D.; O'Sullivan, T. P.; Guiry, P. J., Synthesis of Quinazolinones and Quinazolines. *Tetrahedron*, 2005, 61, 10153-10202.
4. Spirkova, K.; Stankovsky, S., Some Tricyclic Annelated Quinazolines. *Chem. Heterocycl. Compd.* 1995, 31, 1217-1218.
5. Baba, A.; Kawamura, N.; Makino, H.; Ohta, Y.; Taketomi, S.; Sohda, T., Studies on Disease-Modifying Antirheumatic Drugs: Synthesis of Novel Quinoline and Quinazoline Derivatives and Their Anti-inflammatory Effect. *J. Med. Chem.* 1996, 39, 5176-5182.
6. Gama, Y.; Shibuya, I.; Simizu, M., Novel and Efficient Synthesis of 4-Dimethylamino-2-glycosylaminoquinazolines by Cyclodesulfurization of Glycosyl Thioureas with Dimethylcyanamide. *Chem. Pharm. Bull.* 2002, 50 (11), 1517-1519.
7. Wakeling, A. E.; Barker, A. J.; Davies, D. H.; Brown, D. S.; Green, L. R.; Cartlidge, S. A.; Woodburn, J. R., Specific Inhibition of Epidermal Growth Factor Receptor Tyrosine Kinase by 4-Anilinoquinazolines. *Breast Cancer Res Treat* 1996, 38, 67-73.
8. He, L.; Jurs, P. C.; Custer, L. L.; Durham, S. K.; Pearl, G. M., Predicting the Genotoxicity of Polycyclic Aromatic Compounds from Molecular Structure with Different Classifiers. *Chem. Res. Toxicol.* 2003, 16, 1567-1580.
9. (a) Cavazzoni, A.; Alfieri, R. R.; Carmi, C.; Zuliani, V.; Galetti, M.; Fumarola, C.; Frazzi, R.; Bonelli, M.; Bordi, F.; Lodola, A.; Mor, M.; Petronini, P. G., Dual Mechanisms of Action of the 5-Benzylidene-hydantoin UPR1024 on Lung Cancer Cell Lines. *Mol. Cancer Ther.* 2008, 7 (2), 361-370;
(b) Bradbury, R. H., Quinazoline Derivatives as EGF and/or Erbb2 Tyrosine Kinase Inhibitors. European Patent, May 8, 2009, EP 1 877 398 B1.
10. (a) Yamashita, T.; Ino, T.; Miyoshi, H.; Sakamoto, K.; Osanai, A.; Nakamaru-Ogiso, E.; Kita, K., Rhodoquinone Reaction Site of Mitochondrial Complex I, in Parasitic Helminth, Ascaris Suum. *Biochim. Biophys. Acta,* 2004, 1608, 97-103;
(b) Matsumoto, J.; Sakamoto, K.; Shinjyo, N.; Kido, Y.; Yamamoto, N.; Yagi, K.; Miyoshi, H.; Nonaka, N.; Katakura, K.; Kita, K.; Yuzaburo, O., Anaerobic NADH-Fumarate Reductase System Is Predominant in the Respiratory Chain of Echinococcus multilocularis, Providing a Novel Target for the Chemotherapy of Alveolar Echinococcosis. *Antimicrobial Agents and Chemotherapy,* 2008, 164-170.
11. Tobe, M.; Isobe, Y.; Tomizawa, H.; Nagasaki, T.; Aoki, M.; Negishi, T.; Hideya, H., Synthesis and Evaluation of 6-Nitro-7-(1-piperazino)quinazolines: Dual-Acting Compounds with Inhibitory Activities toward Both Tumor Necrosis Factor-a (TNF-a) Production and T Cell Proliferation. *Chem. Pharm. Bull.,* 2003, 51 (9), 1109-1112.
12. (a) Sagiv-Barfi, I.; Weiss, E.; Levitzki, A., Design, Synthesis, and Evaluation of Quinazoline T Cell Proliferation Inhibitors. *Bioorganic & Medicinal Chemistry,* 2010, 18 (17), 6404-6413;
(b) Tobe, M.; Isobe, Y.; Tomizawa, H.; Matsumoto, M.; Obara, F.; Nagasaki, T.; Hayashi, H., Structure-Activity Relationships of Quinazoline Derivatives: Dual-Acting Compounds with Inhibitory Activities toward Both TNF-a Production and T Cell Proliferation. *Bioorganic & Medicinal Chemistry Letters,* 2001, 11 (4), 545-548.
13. de Reijke, T. M.; Klarskov, P., Comparative Efficacy of Two al-Adrenoreceptor Antagonists, Doxazosin and Alfuzosin, in Patients with Lower Urinary Tract Symptoms from Benign Prostatic Enlargement. *BJU International,* 2004, 93 (6), 757-762.
14. Buzelin, J. M.; Fonteyne, E.; Kontturi, M.; Witjes, W. P. J.; Khan, A., Comparison of Tamsulosin with Alfuzosin in the Treatment of Patients with Lower Urinary Tract Symptoms Suggestive of Bladder Outlet Obstruction (Symptomatic Benign Prostatic Hyperplasia). *British Journal of Urology,* 1997, 80 (4), 597-605.
15. (a) Campbell, L.; Blackhall, F.; Thatcher, N., Gefitinib for the Treatment of Non-Small-Cell Lung Cancer. *Expert Opinion on Pharmacotherapy,* 2010, 11 (8), 1343-1357;
(b) Chen, F.; Luo, X.; Zhang, J.; Lu, Y.; Luo, R., Elevated Serum Levels of TPS and CYFRA 21-1 Predict Poor Prognosis in Advanced Non-Small-Cell Lung Cancer Patients Treated with Gefitinib. *Medical Oncology,* 2010, 27 (3), 950-957;
(c) Kook, E. H.; Kim, Y. M.; Kim, H. T.; Koh, J. S.; Choi, Y. J.; Rho, J. K.; Kim, H.-R.; Kim, C. H.; Lee, J. C., Prognostic Value of E-Cadherin Expression in Non-Small Cell Lung Cancer Treated with Gefitinib. *Oncology Research,* 2009, 18 (9), 445-451.
16. (a) Wu, Y.; Liao, M.; Qin, S.; Sun, Y.; Zhou, C., Efficacy and Safety of Erlotinib in the Treatment for Advanced Non-Small Cell Lung Cancer in Chinese Patients. *Zhonghua Zhongliu Zazhi,* 2010, 32 (2), 148-151;
(b) Gridelli, C.; Maione, P.; Bareschino, M. A.; Schettino, C.; Sacco, P. C.; Ambrosio, R.; Barbato, V.; Falanga, M.; Rossi, A., Erlotinib in the Treatment of Non-Small Cell Lung Cancer: Current Status and Future Developments. *Anticancer Research,* 2010, 30 (4), 1301-1310.
17. (a) Rimawi, M. F.; Wiechmann, L. S.; Wang, Y.-C.; Huang, C.; Migliaccio, I.; Wu, M.-F.; Gutierrez, C.; Hilsenbeck, S. G.; Arpino, G.; Massarweh, S.; Ward, R.; Soliz, R.; Osborne, C. K.; Schiff, R., Reduced Dose and Intermittent Treatment with Lapatinib and Trastuzumab for Potent Blockade of the HER Pathway in HER2/neu- Overexpressing Breast Tumor Xenografts. *Clinical Cancer Research*, 2011, 17 (6), 1351-1361;
(b) Bouchalova, K.; Cizkova, M.; Cwiertka, K.; Trojanec, R.; Friedecky, D.; Hajduch, M., Lapatinib in Breast Cancer—The Predictive Significance of HER1 (EGFR), HER2, PTEN and PIK3CA Genes and Lapatinib Plasma Level Assessment. *Biomedical Papers*, 2010, 154 (4), 281-288.
18. Panchasara, D. R.; Pande, S., Synthesis and Biological Activity of 3-Chloro-1-(4-perimidine methylcarbonyl amino)-4-phenyl-azetidin-2-one. *E-Journal of Chemistry*, 2009, 6 (Suppl. 1), S91-S96.
19. Liu, K. C.; Huang, H. S.; Fan, L. T., Synthesis and Biological Evaluation of Some Representative 10-Substituted 9,10-dihydro-8H-imidazo-[1,2-a] and 10-Substituted 8H-1,2,4-triazolo[4,3-a]Perimidine Derivatives. *Zhonghua Yaoxue Zazhi*, 1993, 45 (6), 511-518.
20. Luthin, D. R.; Rabinovich, A. K.; Bhumralkar, D. R.; Youngblood, K. L.; Bychowski, R. A.; Dhanoa, D. S.; May, J. M., Synthesis and Biological Activity of Oxo-7H-benzo[e]perimidine-4-Carboxylic Acid Derivatives as Potent, Nonpeptide Corticotropin Releasing Factor (CRF) Receptor Antagonists. *Bioorganic & Medicinal Chemistry Letters*, 1999, 9 (5), 765-770.
21. (a) Tian, M.; Ito, Y.; Nakaso, M.; Matsubara, T.; Watanabe, M.; Hasegawa, S.; Furuki, M.; Hirokawa, K. Perimidine-type Squarylium Compound as Efficient Near-IR-Absorbing Dye, Imaging Material Therefrom, and Image Formation Method Thereby. *Jpn. Kokai Tokkyo Koho*, 2010184975A, Aug. 26, 2010;
(b) Hase, T. Perimidine Dyes Showing Visible Light and Near-IR Absorption. *Jpn. Kokai Tokkyo Koho*, 2005015750A, Jan. 20, 2005.
22. (a) Bauer, W.; Akram, M.; Deutz, H. Oxidative Hair Dyes and Perimidine Couplers Therefor. *Ger. Offen.* 19514996A1, Oct. 31, 1996;
(b) Hirokawa, K.; Anazawa, K.; Ito, Y.; Tian, M.; Nakaso, S.; Hasegawa, S.; Matsubara, T.; Furuki, M.; Watanabe, M.; Miyahara, T. Perimidine-substituted Squarylium Dye, Dispersion Medium, Detection Medium and Image Forming Material. U.S. Pat. Appl. Publ. 20100108949A1, May 6, 2010;
(c) Kaneko, Y.; Kita, H.; Ikesu, S. (Phenylimino) perimidine Dyes for Thermal-Transfer Recording Materials. *Jpn. Kokai Tokkyo Koho*, 04283271A, Oct. 8, 1992.
23. Kaegi, H. H.; Burger, W.; Bader, G. J., The Synthesis of 7-Chloro-1-methyl-5-phenyl-1,3-dihydro-2H-1,4-benzodiazepin-2-one-5-14C and 7-Nitro-1-methyl-5-(2'-fluorophenyl)-1,3-dihydro-2H-1,4-benzodiazepin-2-one-5-14C. *J. Labelled Compd. Radiopharm.* 1982, 19 (2), 289-299.
24. Rossi, E.; Calabrese, D.; Farma, F., A Convenient Synthesis of Quinazoline Ring by Tandem Aza-Wittig Reaction/Lectrocyclic Ring Closure. *Tetrahedron*, 1991, 47 (30), 5819-5834.
25. Sauer, J.; Mayer, K. K., Thermolysis and Photolysis of 3,4-Diphenyl-Δ²-1,2,4-oxadiazolin-5-one and 2,4-Diphenyl-Δ2-1,3,4-oxadinazolin-5-one. *Tetrahedron Lett.* 1968, (3), 325-330.
26. Fuhrer, W.; Gschwend, H. W., Ortho Functionalization of Aromatic Amines: Ortho Lithiation of N-Pivaloylanilines. *J. Org. Chem.* 1979, 44 (7), 1133-1136.
27. Bergman, J.; Brynolf, A.; Bjorn, E.; Vuorinen, E., Synthesis of Quinazolines. *Tetrahedron*, 1986, 42, 3697-3706.
28. Kofanov, E. R.; Sosnina, V. V.; Danilova, A. S.; Korolev, P. V., Synthesis of Substituted 2,4-Diarylquinazolines. *Zhurnal Prikladnoi Khimii (Sankt-Peterburg)*, 1999, 72 (5), 813-815.
29. Schmidt, R. R.; Schneider, W.; Karg, J.; Burkert, U., Thermolysis of Diazonium Ions. III. Synthesis of Heterocycles by Thermolysis of O-Substituted Aromatic Diazonium Ions. *Chem. Ber.* 1972, 105 (5), 1634-1635.
30. Gasparic, J.; Zimak, J.; Sedmera, P.; Breberova, Z.; Volke, J., Products of the Acid Hydrolysis of 7-Chloro-1,3-dihydro-3-hydroxy-5-phenyl-2H-1,4-benzodiazepin-2-one (oxazepam). *Collection of Czechoslovak Chemical Communications*, 1979, 44 (7), 2243-2249.
31. Natsugari, H.; Meguro, K.; Kuwada, Y., Heterocycles. XII. Synthesis of 2-Amino-5-phenyl-1,4-benzodiazepine 1-Oxides and 2-Amino-6-phenyl-1,5-benzodiazocine 1-Oxides and Their Reactions with Acylating Agents. *Chemical & Pharmaceutical Bulletin*, 1979, 27 (11), 2608-2617.
32. Kovac, T.; Belin, B.; Fajdiga, T.; Sunjic, V., New Synthesis of 7-Bromo-1,3-dihydro-3-hydroxy-5-(2'-pyridyl)-2H-1,4-benzodiazepin-2-one. *Journal of Heterocyclic Chemistry*, 1981, 18, 59-62.
33. Hromatka, O.; Knollmueller, M.; Binder, D., Syntheses of 1,3-Dihydro-2,1,4-benzothiadiazepines. *Monatsh. Chem.* 1969, 100 (3), 872-878.
34. Natsugari, H.; Meguro, K.; Kuwada, Y., Heterocycles. XI. Synthesis of 2-Amino-6-phenyl-3,4-dihydro-1,5-benzodiazocines. *Chem. & Pharm. Bull.*, 1979, 27 (11), 2589-2595.
35. Stempel, A.; Douvan, I.; Reeder, E.; Sternbach, L. H., Quinazolines and 1,4-Benzodiazepines. XXXIV. 4,1,5-Benzoxadiazocin-2-ones, A Novel Ring System. *Journal of Organic Chemistry*, 1967, 32 (8), 2417-2425.
36. Fryer, R. I.; Earley, J. V.; Sternbach, L. H., Quinazolines and 1,4-Benzodiazepines. XXXVII. Synthesis and Rearrangements of Substituted 5-Phenyl-1H-1,4-benzodiazepine. *Journal of Organic Chemistry*, 1967, 32 (12), 3798-3803.
37. Giraldi, P. N.; Fojanesi, A.; Tosolini, G. P.; Dradi, E.; Logemann, W., Synthesis and Reaction of A New Benzoxadiazocine Structure. *Journal of Heterocyclic Chemistry*, 1970, 7 (6), 1429-1431.
38. Hunter, D.; Neilson, D. G.; Weakley, T. J. R., Rearrangement Reactions of 1,3,6-Triaryl-1,4-dihydro-s-tetrazines Leading to 2,4-Diarylquinazolines, 1-Anilino-3,5-diaryl-1H-1,2,4-triazoles, 1,3,5-Triaryl-1H-1,2,4-triazoles, and 2,5-Diaryl-1H-1,3,4-oxadiazoles. X-Ray Structure Determination of 6-Isopropyl-2,4-diphenylquinazoline. *J. Chem. Soc., Perkin Trans.* 1, 1985, (12), 2709-2712.
39. Ohta, K.; Nakamura, Y.; Iwaoka, J.; Nomura, Y., Synthesis of Quinazoline Derivatives by the [4+2] Cycloaddition of 2,1-Benzisoxazoles with 3-Imidazoline-2,5-diones. *Nippon Kagaku Kaishi*, 1990, (1), 72-83.
40. Bell, S. C.; Wei, P. H. L., Ring Closure Reactions with Nitriles. II. Formation of Pyrrolo[1,2-a]quinazolines and Thiazolo[3,2-a]quinazolines. *Journal of Heterocyclic Chemistry*, 1968, 5 (2), 185-190.
41. Katritzky, A. R.; Yang, B.; Jiang, J.; Steel, P. J., Ring-Opening Rearrangements of 2-(Benzotriazol-1-yl) Enamines and a Novel Synthesis of 2,4-Diarylquinazoline. *Journal of Organic Chemistry*, 1995, 60 (1), 246-249.
42. Dusemund, J., Reactions of 1-Aminothioxanthone-6,6-dioxides with Formamide. *Arch. Pharm.* (Weinheim, Ger.) 1975, 308 (3), 230-234.
43. Kim, J.-H.; Nam, S.-U., Synthesis of New (4-Phenyl-2-quinazolyl)acetonitrile Derivatives. *Journal of the Korean Chemical Society*, 2003, 47 (4), 417-422.
44. (a) Song, Y.-H.; Yeh, S.-J.; Chen, C.-T.; Chi, Y.; Liu, C.-S.; Yu, J.-K.; Hu, Y.-H.; Chou, P.-T.; Peng, S.-M.; Lee, G.-H., Bright and Efficient, Non-Doped, Phosphorescent Organic Red-Light-Emitting Diodes. *Advanced Functional Materials,* 2004, 14 (12), 1221-1226;
(b) Uff, B. C.; Joshi, B. L.; Popp, F. D., Reissert compound studies. Part LV. Studies with Reissert Compounds. Part 17. Mono-Reissert Compound Formation at the 1,2-Position of the Quinazoline System. *Journal of the Chemical Society, Perkin Transactions* 1, 1986, (12), 2295-2303;
(c) Byford, A.; Goadby, P.; Hooper, M.; Kamath, H. V.; Kulkarni, S. N., o-Aminophenyl Alkyl/Aralkyl Ketones and Their Derivatives. Part V. An Efficient Synthetic Route to Some Biologically Active 4-Substituted Quinazolines. *Indian Journal of Chemistry,* 1988, 27B (4), 396-397.
45. Hoefnagel, A. J.; van Koningsveld, H.; van Meurs, F.; Peters, J. A.; Sinnema, A.; van Bekkum, H., Reactions of Hydroxyglycines. New Synthetic Routes to 4-Phenylquinazoline Derivatives. *Tetrahedron,* 1993, 49 (31), 6899-6912.
46. Blazevic, N.; Oklobdzija, M.; Sunjic, V.; Kajfez, F.; Kolbah, D., New Ring Closures of Quinazoline Derivatives by Hexamine. *Acta Pharmaceutica Jugoslavica,* 1975, 25 (4), 223-230.
47. Kunz, M. A.; Koberle, K. Anthrapyrimidines. *Ger. Offen.* Apr. 4, 1934.
48. Schlichting, O. Anthrapyrimidine Derivative. *Ger. Offen.* Dec. 16, 1936.
49. Kunz, M. A.; Koberle, K.; Schlichting, O. Process for Preparing Compounds of Anthrapyrimidines. *Ger. Offen.* 693478, Jul. 15, 1931.
50. Weidinger, H.; Eilingsfeld, H.; Haese, G. Process for Preparing Anthrapyrimidines. *Ger. Offen.* 1159456, Dec. 19, 1963.
51. Weidinger, H.; Eilingsfeld, H.; Haese, H. G. Substituted Anthrapyrimidines. *Ger. Offen.* 1237122, Mar. 23, 1967.
52. Eilingsfeld, H.; Schwantje, G. Anthrapyrimidine Dyes. *Ger. Offen.* 2124589, Nov. 30, 1972.
53. Schroeder, B.; Neeff, R.; Claussen, U. Anthrapyrimidine Derivatives as Dyes. *Ger. Offen.* 3001188, Jul. 16, 1981.

What is claimed is:

1. A method for forming a quinazoline derivative, comprising the steps of:
   providing thiourea as a reagent;
   providing a starting material comprising a 2-aminoarylcarbonyl compound, wherein the 2-aminoarylcarbonyl compound has a structure of:

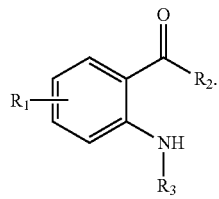

wherein $R_1$ is independently selected from H, F, Cl, Br, I, $NO_2$, $CF_3$, alkyl, and aryl groups, wherein $R_1$ is present at any one, any two, any three, or all four available ring positions, wherein $R_2$ is an aryl or alkyl group of less than two α-hydrogen atoms, and wherein $R_3$ is selected from H, alkyl, C(O)alkyl, C(O)aryl, and $C(O)NMe_2$;
mixing said thiourea and said starting material to form a mixture; and
reacting said mixture in a solvent of high boiling point, said solvent selected from the group consisting of water, DMF, DMSO, ethylene glycol, 2-methoxyethanol, diethylene glycol monoethyl ether, p-dichlorobenzene, and combinations thereof at a temperature ranging from 75° C. to 185° C. to yield said quinazoline derivative, wherein said quinazoline derivative has a structure selected from:

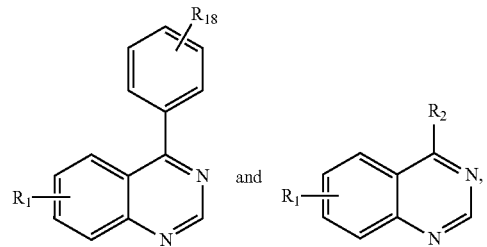

wherein $R_1$ and $R_{18}$ are independently selected from H, F, Cl, Br, I, $NO_2$, $CF_3$, alkyl, and aryl groups, wherein $R_1$ is present at any one, any two, any three, or all four available ring positions and $R_{18}$ is present at any one, any two, any three, any four, or all five available ring positions, and wherein $R_2$ is an alkyl group of less than two α-hydrogen atoms.

2. The method of claim 1, wherein at least one $R_1$ is an aryl group, and wherein said aryl group is attached via a single carbon-carbon bond.

3. The method of claim 1, wherein said starting material is 2-aminobenzophenone, 2-amino-2',5-dichlorobenzophenone, 2-amino-5-nitrobenzophenone, or 2-amino-4-methylbenzophenone.

4. The method of claim 1, wherein at least one $R_{18}$ is an aryl group, and wherein said aryl group is attached via a single carbon-carbon bond.

5. A method for forming a heterocyclic aromatic compound, comprising the steps of:
   providing thiourea as a reagent;
   providing a starting material comprising an aromatic compound, wherein the aromatic compound has a structure selected from:

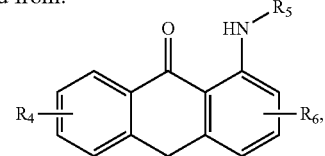

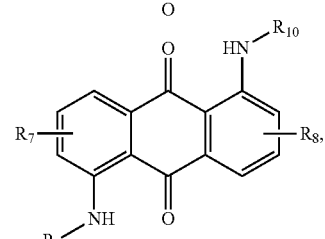

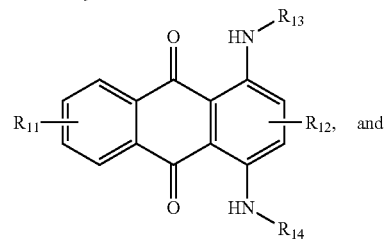

-continued

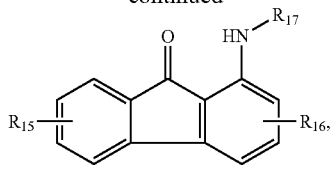

wherein $R_4$, $R_7$, $R_{11}$, $R_{15}$, and $R_{16}$ are independently selected from F, Cl, Br, I, $NO_2$, $CF_3$, alkyl, and aryl groups, wherein $R_5$, $R_9$, $R_{10}$, $R_{13}$, $R_{14}$, and $R_{17}$ are independently selected from alkyl, C(O)alkyl, C(O)aryl, and C(O)NMe$_2$, wherein $R_6$, $R_8$, and $R_{12}$, are independently selected from F, Cl, Br, I, OH, $SO_3H$, alkyl, and aryl groups, and wherein $R_4$, $R_6$, $R_7$, $R_8$, $R_{11}$, $R_{12}$, $R_{15}$, and $R_{16}$ are present at least once at any available ring position;

mixing said thiourea and said starting material to form a mixture; and reacting said mixture in a solvent of high boiling point, said solvent selected from the group consisting of water, DMF, DMSO, ethylene glycol, 2-methoxyethanol, diethylene glycol monoethyl ether, p-dichlorobenzene, and combinations thereof at a temperature ranging from 75° C. to 185° C. to yield said heterocyclic aromatic compound, wherein said heterocyclic aromatic compound is selected from:

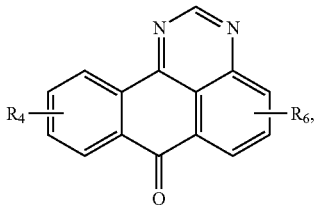

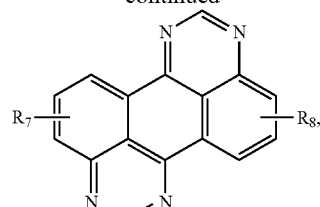

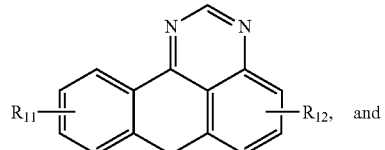

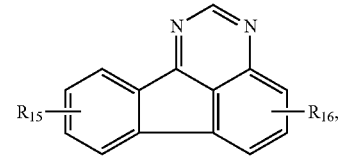

wherein $R_4$, $R_7$, $R_{11}$, $R_{15}$, and $R_{16}$ are independently selected from F, Cl, Br, I, $NO_2$, $CF_3$, alkyl, and aryl groups, wherein $R_6$, $R_8$, and $R_{12}$ are independently selected from F, Cl, Br, I, OH, $SO_3H$, alkyl, and aryl groups, and wherein $R_4$, $R_6$, $R_7$, $R_5$, $R_{11}$, $R_{12}$, $R_{15}$, and $R_{16}$ are present at least once at any available ring position.

6. The method of claim 1, wherein said quinazoline derivative is 4-phenyl-quinazoline, 2',6-dichloro-4-phenyl-quinazoline, 4-phenyl-6-nitro-quinazoline, or 4-phenyl-7-methyl-quinazoline.

* * * * *